(12) United States Patent
Kini et al.

(10) Patent No.: US 12,024,492 B2
(45) Date of Patent: Jul. 2, 2024

(54) PROCESS FOR PREPARATION OF AZOXYSTROBIN AND INTERMEDIATES THEREOF

(71) Applicant: UPL LIMITED, Mumbai (IN)

(72) Inventors: Prashant Vasant Kini, Mumbai (IN); Santosh Ganpat Shelke, Mumbai (IN)

(73) Assignee: UPL LTD, Mumbai (IN)

( * ) Notice: Subject to any disclaimer, the term of this patent is extended or adjusted under 35 U.S.C. 154(b) by 158 days.

(21) Appl. No.: 17/603,516

(22) PCT Filed: Apr. 17, 2020

(86) PCT No.: PCT/IB2020/053641
§ 371 (c)(1),
(2) Date: Oct. 13, 2021

(87) PCT Pub. No.: WO2020/212919
PCT Pub. Date: Oct. 22, 2020

(65) Prior Publication Data
US 2022/0185784 A1    Jun. 16, 2022

(30) Foreign Application Priority Data
Apr. 18, 2019 (IN) .............................. 201921015652

(51) Int. Cl.
*C07D 239/52* (2006.01)
(52) U.S. Cl.
CPC .................................. *C07D 239/52* (2013.01)
(58) Field of Classification Search
CPC ............................. C07D 239/52; C07D 487/04
See application file for complete search history.

(56) References Cited

U.S. PATENT DOCUMENTS

| 6,103,717 A | 8/2000 | Heinemann et al. |
| 2015/0011753 A1 | 1/2015 | Hindupur et al. |
| 2016/0200687 A1 | 7/2016 | Chen et al. |

FOREIGN PATENT DOCUMENTS

| CN | 102311392 A | 1/2012 |
| EP | 0382375 B1 | 3/1994 |
| EP | 2998299 A1 | 3/2016 |
| KR | 20140085204 A | 7/2014 |
| WO | 2008043978 A1 | 4/2008 |
| WO | 201490997 A1 | 12/2014 |
| WO | 2017060917 A1 | 4/2017 |

OTHER PUBLICATIONS

KR1020140085204 (translated Patent Application from Korean Intellectual Property Office) 2014.*
Heinemann, U. et al.; "Fluoxastrobin (HEC 5725)—the new dimension in strobilurin fungicides"; Pflanzenschutz-Nachrichten Bayer, vol. 57, Issue No. 3; 2004; pp. 299-318.
International Search Report and Written Opinion for International Application PCT/IB2020/053641; International Filing Date: Apr. 17, 2020; Date of Mailing: Jun. 19, 2020; 13 pages.
International Search Report and Written Opinion for International Application PCT/IB2020/053656; International Filing Date: Apr. 17, 2020; Date of Mailing: Jul. 14, 2020; 13 pages.
Liu, Y-G. et al.; "A Concise Synthesis of Azoxystrobin using a Suzuki Cross-Coupling Reaction"; Journal of Chemical Research, vol. 39; 2015; pp. 586-589.

* cited by examiner

Primary Examiner — Deepak R Rao
(74) Attorney, Agent, or Firm — CANTOR COLBURN LLP

(57) ABSTRACT

The present invention relates to a process for preparation of strobilurin compound, azoxystrobin and its intermediates using a catalyst selected from 1,8-Diazabicyclo[5.4.0]undec-7-ene or 1,5-Diazabicyclo[4.3.0]non-5-ene, salts thereof, or derivatives thereof.

20 Claims, No Drawings

PROCESS FOR PREPARATION OF AZOXYSTROBIN AND INTERMEDIATES THEREOF

CROSS REFERENCE TO RELATED APPLICATIONS

This application is a National Stage application of PCT/IB2020/053641, filed Apr. 17, 2020, which claims the benefit of priority to Indian Patent Application 201921015652, filed Apr. 18, 2019, both of which are incorporated by reference in their entirety herein.

FIELD OF INVENTION

The present invention relates to a process for preparation of strobilurin compound. More particularly the present invention a process for preparation of azoxystrobin and processes for preparation of intermediate compounds useful for preparation of azoxystrobin.

BACKGROUND OF THE INVENTION

Strobilurins are broad spectrum fungicides and are widely used pesticides both in foliar application and in seed treatment. Due to their wide spectrum activity profile, strobilurins are important class of fungicides. Notable amongst this class of compounds are azoxystrobin, trifloxystrobin, fluoxastrobin, and picoxystrobin.

EP 382375 discloses various derivatives of propenoic acid useful as fungicides, including azoxystrobin. This patent also discloses process for preparation of azoxystrobin and intermediates thereof.

WO2008043978 discloses a process for the preparation of azoxystrobin using 1,4-diazabicyclo [2.2.2] octane (DABCO) as a catalyst.

WO2017060917 discloses a process for the preparation of azoxystrobin by reacting o-cyanophenol with methyl 3-methoxy (2-(2-(6-chloropyrimidine)-4-yl) oxyphenyl) acrylate in the presence of a catalyst selected form a group of crown ethers or polyethylene glycol (PEG).

The prior art processes for the preparation of azoxystrobin provide the intermediate and final compounds in low yield and low purity. However, the need for a new efficient, scalable and cost-effective methods for the synthesis of azoxystrobin still remains.

The present inventors surprisingly found that the process for preparation of azoxystrobin and intermediates thereof using diazabicyclo undec-7-ene and diazabicyclo non-5-ene compounds as catalyst, provide the desired compounds in high yield and with high purity substantially free from impurities.

OBJECT OF THE INVENTION

It is an object of the present invention to provide a process for the preparation of strobilurin compounds and intermediates thereof.

It is an object of the present invention to provide a process for the preparation of azoxystrobin.

It is an object of the present invention to provide a process for the preparation of useful intermediates for preparation of strobilurin compounds.

It is an object of the present invention to use of 1,8-diazabicyclo[5.4.0]undec-7-ene (DBU) or 1,5-diazabicyclo[4.3.0]non-5-ene (DBN) or salts thereof or derivatives thereof for preparation of strobilurin compounds.

It is an object of the present invention to provide an efficient process for the preparation of azoxystrobin which significantly improve the purity of azoxystrobin.

It is another object of the present invention to provide a process for reducing the impurity generated in the process for the preparation of azoxystrobin and its intermediates.

It is an object of the present invention to provide azoxystrobin and intermediates thereof that are substantially free from impurities.

SUMMARY OF THE INVENTION

In an aspect the present invention provides a process for preparation of a strobilurin compounds and intermediates thereof.

In another aspect the present invention provides a process for preparation of compound of Formula (I) using diazabicyclo compounds as catalyst, particularly selected from 1,8-diazabicyclo[5.4.0]undec-7-ene (DBU) or 1,5-diazabicyclo[4.3.0]non-5-ene (DBN) or salts thereof or derivatives thereof.

(I)

In another aspect the present invention provides a process for the preparation of intermediate compounds of formula (II) and formula (VI) which are useful for the preparation of azoxystrobin of compound of formula (I).

In an aspect the present invention provides a process for preparation of compound of formula (I)

(I)

comprising:
reacting a compound of formula (II) with compound of formula (III)

(II)

(III)

in the presence of a catalyst selected from 1,8-Diazabicyclo[5.4.0]undec-7-ene or 1,5-Diazabicyclo [4.3.0]non-5-ene or salts and derivatives thereof, wherein Q is selected from methyl (E)-2-(3-methoxy) acrylate and methyl 2-(3,3-dimethoxy) propanoate.

In another aspect the present invention provides a process for preparation of compound of formula (I)

(I)

comprising:

reacting compound of formula (VI) with compound of formula (V)

(VI)

(V)

in the presence of a catalyst selected from 1,8-diazabicyclo[5.4.0]undec-7-ene or 1,5-diazabicyclo[4.3.0]non-5-ene or salts thereof or derivatives thereof.

In an aspect the present invention provides a process for preparation of compound of formula (II)

(II)

comprising:

reacting a compound of formula (V) with a compound of formula (IV)

(V)

(IV)

in the presence of a catalyst selected from 1,8-Diazabicyclo[5.4.0]undec-7-ene, salts and derivatives thereof or 1,5-Diazabicyclo[4.3.0]non-5-ene or salts thereof or derivatives thereof;

wherein Q is selected from methyl (E)-2-(3-methoxy) acrylate and methyl 2-(3,3-dimethoxy) propanoate.

In another aspect the present invention provides a process for preparation of compound of formula (VI)

(VI)

comprising reacting a compound of formula (IV) with a compound of formula (III)

(IV)

(III)

in the presence of a catalyst selected from 1,8-diazabicyclo[5.4.0]undec-7-ene or 1,5-diazabicyclo[4.3.0]non-5-ene or salts thereof or derivative compounds thereof.

In an aspect the present invention relates to process for preparation compound of formula (I)

(I)

comprising:

(i) reacting compound of formula (IV) with compound of formula (V) in the presence of a catalyst selected from 1,8-Diazabicyclo[5.4.0]undec-7-ene, salts and derivatives thereof or 1,5-Diazabicyclo[4.3.0]non-5-ene, salts and derivatives thereof to obtain compounds of formula (II) wherein Q is as defined as above ; and (ii) reacting compounds of formula (II) with compound of formula (III)

in the presence of a catalyst selected from 1,8-Diazabicyclo[5.4.0]undec-7-ene or salts thereof or derivatives thereof or 1,5-Diazabicyclo[4.3.0]non-5-ene to obtain compound of formula (I).

In another aspect the present invention provides a process for preparation compound of formula (I)

comprising:
(i) reacting compound of formula (IV) with compound of formula (III) in the presence of a catalyst selected from 1,8-Diazabicyclo[5.4.0]undec-7-ene, salts and derivatives thereof or 1,5-Diazabicyclo[4.3.0]non-5-ene, salts and derivatives thereof to obtain compound of formula (VI); and (ii) reacting compound of (VI) with compound of formula (V)

in the presence of a catalyst selected from 1,8-Diazabicyclo[5.4.0]undec-7-ene, salts and derivatives thereof or 1,5-Diazabicyclo[4.3.0]non-5-ene, salts thereof or derivatives thereof to obtain compound of formula (I).

In another aspect the present invention provides use of a catalyst selected from 1,8-Diazabicyclo[5.4.0]undec-7-ene, salts thereof or derivatives thereof or 1,5-Diazabicyclo[4.3.0]non-5-ene, salts thereof or derivatives thereof for proceeding a process for preparation azoxystrobin of formula (I).

In an aspect the present invention provides azoxystrobin of formula (I) with high purity substantially free from impurities.

In an aspect the present invention provides intermediate compounds of formula (II) and formula (VI) substantially free of impurities which are useful for the preparation of highly pure azoxystrobin.

DETAILED DESCRIPTION OF THE INVENTION

These and other features, aspects and advantages of the present invention may be further understood and/or illustrated when the following detailed description.

For the purposes of the following detailed description, it is to be understood that the invention may assume various alternative variations and step sequences, except where expressly specified to the contrary. Moreover, other than in any operating examples, or where otherwise indicated, all numbers expressing, for example, quantities of materials/ingredients used in the specification are to be understood as being modified in all instances by the term "about".

Thus, before describing the present invention in detail, it is to be understood that this invention is not limited to particularly exemplified systems or process parameters that may of course, vary. It is also to be understood that the terminology used herein is for the purpose of describing particular embodiments of the invention only, and is not intended to limit the scope of the invention in any manner.

The use of examples anywhere in this specification including examples of any terms discussed herein is illustrative only, and in no way limits the scope and meaning of the invention or of any exemplified term. Likewise, the invention is not limited to various embodiments given in this specification. Unless otherwise defined, all technical and scientific terms used herein have the same meaning as commonly understood by one of ordinary skill in the art to which this invention pertains. In the case of conflict, the present document, including definitions will control.

It must be noted that, as used in this specification, the singular forms "a," "an" and "the" include plural referents unless the content clearly dictates otherwise. The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

As used herein halogen includes chlorine, bromine, iodine, and fluorine.

As used herein, alkali metal includes lithium, sodium, potassium, etc.

As used herein, the terms "comprising" "including," "having," "containing," "involving," and the like are to be understood to be open-ended, i.e., to mean including but not limited to.

The present invention provides a simple, commercially and industrially viable process for the preparation of strobilurin compounds. The present invention provides the strobilurin compounds of Formula (I) in good yield and high purity. The catalyst used in the present process facilitates complete conversion of reactants to the desired product and simultaneously reducing the formation of undesired products/impurity.

The inventors of the present invention have surprisingly found that the strobilurin compounds of Formula (I) that are substantially free of certain impurities can be prepared in excellent yield when the reaction proceed in presence of a catalyst selected from 1,8-Diazabicyclo[5.4.0]undec-7-ene, salts and derivatives thereof or 1,5-Diazabicyclo[4.3.0]non-5-ene, salts thereof or derivatives thereof. Hereunder described are the embodiments of the present invention in detail.

In an aspect, the present invention provides process for the preparation of strobilurin compounds of Formula (I) using a catalyst selected from 1,8-Diazabicyclo[5.4.0]undec-7-ene, salts thereof or derivatives thereof or 1,5-Diazabicyclo[4.3.0]non-5-ene, salts thereof or derivatives thereof.

In an embodiment, there is provided a process for the preparation of key intermediates of compounds of Formula (II) and (VI) for making strobilurin compounds of Formula (I) wherein the process is carried out in the presence of a catalyst selected from 1,8-Diazabicyclo[5.4.0]undec-7-ene, salts thereof or derivatives thereof or 1,5-Diazabicyclo[4.3.0]non-5-ene, salts thereof or derivatives thereof.

In an aspect, the present invention provides process for the preparation of azoxystrobin (I) using a catalyst selected from 1,8-Diazabicyclo[5.4.0]undec-7-ene, salts and derivatives thereof or 1,5-Diazabicyclo[4.3.0]non-5-ene, salts thereof or derivatives thereof.

In yet another embodiment, the process for the preparation of azoxystrobin proceeds via the compound of Formula (II) in presence of a catalyst selected from 1,8-Diazabicyclo [5.4.0]undec-7-ene, salts thereof or derivatives thereof or 1,5-Diazabicyclo [4.3.0]non-5-ene, salts thereof or derivatives thereof.

In an embodiment the catalyst 1,8-Diazabicyclo[5.4.0]undec-7-ene or salts and derivatives thereof or 1,5-Diazabicyclo[4.3.0]non-5-ene or salts thereof or derivatives thereof is used in an amount from about 0.01 mol % to about 7 mol %.

In a further embodiment the catalyst 1,8-Diazabicyclo[5.4.0]undec-7-ene, salts and derivatives thereof or 1,5-Diazabicyclo[4.3.0]non-5-ene salts thereof or derivatives thereof is used in an amount from about 0.1 mol % to about 5 mol %.

The process of the present invention is carried out in the presence of a catalytic amount of 1,8-Diazabicyclo[5.4.0]undec-7-ene or 1,5-Diazabicyclo[4.3.0]non-5-ene or salts thereof or derivatives thereof, preferably between 0.01 and 7 mol % of that is more than 0.01 but less than 7 mol %, significantly in smaller amounts. Preferably, the process is carried out in the presence of between 0.1 and 7 mol % of 1,8-Diazabicyclo [5.4.0]undec-7-ene or 1,5-Diazabicyclo [4.3.0]non-5-ene or salts and derivatives thereof. Any amount of 1,8-Diazabicyclo[5.4.0]undec-7-ene or 1,5-Diazabicyclo[4.3.0]non-5-ene or salts thereof or derivatives thereof between 0.1 and 5 mol % is suitable, but the invention provides especial benefit in that the amount of catalyst used may be between 0.1 and 2 mol %.

In general, the reaction may be carried out at a temperature of from 0 to 120° C., suitably at a temperature of from 40 to 100° C., and typically at a temperature of from 45 to 95° C., for example, from 60 to 85° C.

In an embodiment, the process for preparation of azoxystrobin involves using 1,8-diazabicyclo[5.4.0]undec-7-ene and derivatives thereof represented by formula (VIII), formula (VIIIa) or formula (VIIIb) as a catalyst;

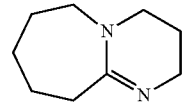

(VIII)

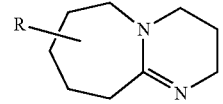

(VIIIa)

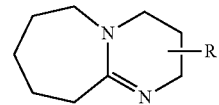

(VIIIb)

wherein R is selected from hydrogen, hydroxyl, $C_1$-$C_{20}$ hydrocarbonyl, amino, $C_1$-$C_6$ alkyl amino, cyano or halogen wherein $C_1$-$C_{20}$ hydrocarbonyl is unsubstituted or substituted, wherein the substituent is independently selected from the group consisting of straight chain hydrocarbonyl, cyclic hydrocarbonyl, saturated hydrocarbonyl and unsaturated hydrocarbonyl. The saturated hydrocarbonyl can be for example, any of methyl, ethyl, propyl, isopropyl, n-butyl, isobutyl, tert-butyl, amyl, and hexyl, and the unsaturated hydrocarbonyl can be for example any of propenyl, isopropenyl, butenyl, isobutenyl, pentenyl, and hexenyl, $C_1$-$C_6$ alkyl amino is unsubstituted or mono or di substituted, for example methylamino, dimethyl amino, diethyl amino, diisopropyl and halogen includes fluorine, chlorine, or bromine.

In an aspect, 1,8-Diazabicyclo[5.4.0]undec-7-ene includes its salts.

Salts of 1,8-Diazabicyclo[5.4.0]undec-7-ene include inorganic salts and organic salts. Inorganic salts include hydrochloride, sulphate, nitrate and phosphate. Organic salts can be selected from the group comprising format, acetate, benzoate, trifluoroacetate, citrate, succinate, maleate, fumarate and oxalate.

In one preferred embodiment the present invention provides a process for the preparation of azoxystrobin using catalytic amount of 1,8-diazabicyclo[5.4.0]undec-7-ene represented by formula (VIII).

In an aspect the present invention provides a process for preparation of azoxystrobin using 1,5-diazabicyclo[4.3.0]non-5-ene and derivative compound thereof represented by formula (IX), formula (IXa) or formula (IXb) as a catalyst.

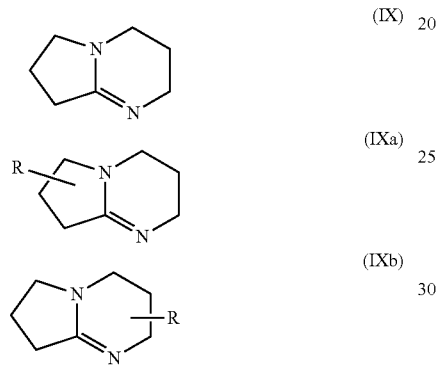

wherein R is selected from hydrogen, hydroxyl, $C_1$-$C_{20}$ hydrocarbonyl, amino, methylamino, dimethyl amino, diethyl amino, diisopropyl, cyano, fluorine, chlorine, or bromine, sulfhydryl, thiocarbonyl, cycloalkyl thioether, cycloalkoxyl or ketal.

wherein, $C_1$-$C_{20}$ hydrocarbonyl comprises straight chain hydrocarbonyl, cyclic hydrocarbonyl, saturated hydrocarbonyl and unsaturated hydrocarbonyl. The saturated hydrocarbonyl can be any of methyl, ethyl, propyl, isopropyl, n-butyl, isobutyl, tert-butyl, amyl, and hexyl, and the unsaturated hydrocarbonyl can be any of propenyl, isopropenyl, butenyl, isobutenyl, pentenyl, and hexenyl.

In another aspect, 1,5-Diazabicyclo[4.3.0]non-5-ene includes salts and derivatives thereof.

The salts of 1,5-Diazabicyclo[4.3.0]non-5-ene include an inorganic salts and organic salts. Inorganic salts include hydrochloride, sulphate, nitrate and phosphate. Organic salts include format, acetate, benzoate, trifluoroacetate, citrate, succinate, maleate, fumarate and oxalate.

In one preferred embodiment the present invention provides a process for the preparation of azoxystrobin using catalytic amount of 1,5-Diazabicyclo[4.3.0]non-5-ene represented by formula (IX).

In yet another aspect, the present invention provides a process for preparation of intermediate compounds of formula (II) and formula (VI) using 1,8-diazabicyclo[5.4.0]undec-7-ene or salts and derivatives thereof or 1,5-diazabicyclo[4.3.0]non-5-ene salts thereof, or derivatives thereof as a catalyst.

In a preferred embodiment, 1,8-Diazabicyclo[5.4.0]undec-7-ene or 1,5-Diazabicyclo[4.3.0]non-5-ene is used as catalyst for preparation of compound of formula (I) or intermediates thereof.

In an embodiment, the process for preparation compound of formula (I)

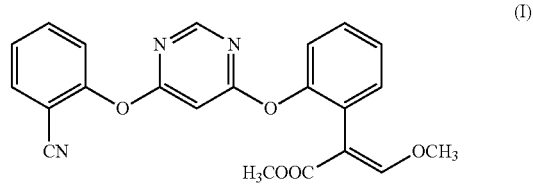

comprising:

reacting compounds of formula (II), wherein Q is as defined above, with the compound of formula (III)

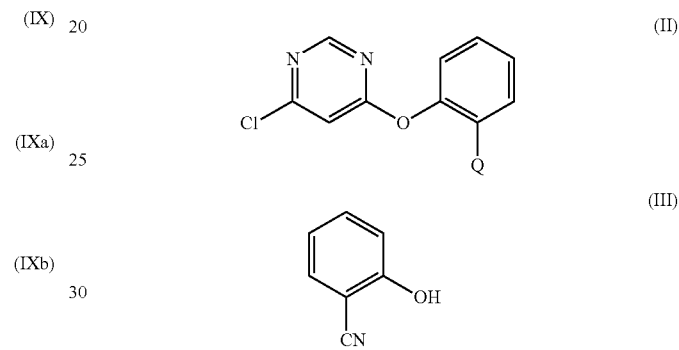

in the presence of a catalyst selected from 1,8-Diazabicyclo[5.4.0]undec-7-ene, salts thereof, or derivatives thereof or 1,5-Diazabicyclo[4.3.0]non-5-ene salts thereof, or derivatives thereof.

In an embodiment, the process according to the present invention is carried out using a compound of formula (II) wherein Q is methyl (E)-2-(3-methoxy)acrylate group (Formula IIa).

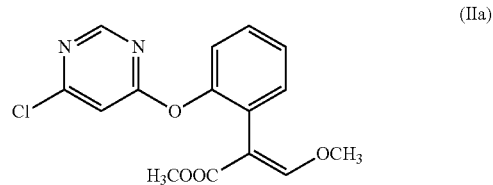

In yet another embodiment, the process according to the present invention is carried out using a mixture of compounds of formula (IIa) and formula (IIb).

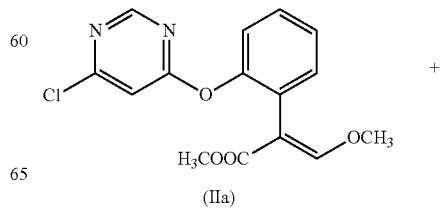

(IIa)

-continued

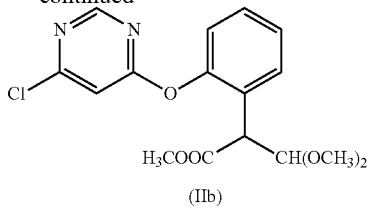

(IIb)

With respect to the present invention a mixture of compound of formula (IIa) and compound of formula (IIb) can be converted to compound of formula (IIa) by known methods.

In an embodiment, the process for preparation of compound of formula (I)

(I)

comprising:
reacting compounds of formula (IIa) with the compound of formula (III)

(IIa)

(III)

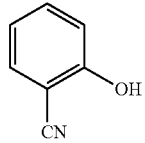

in the presence of a catalyst selected from 1,8-Diazabicyclo[5.4.0]undec-7-ene, salts and derivatives thereof or 1,5-Diazabicyclo[4.3.0]non-5-ene salts thereof, or derivatives thereof.

In an embodiment, the process for preparation compound of formula (I)

(I)

comprising:
reacting a mixture of compounds of formula (IIa) and compound (IIb) with the compound of formula (III)

(III)

in the presence of a catalyst selected from 1,8-Diazabicyclo[5.4.0]undec-7-ene, salts and derivatives thereof or 1,5-Diazabicyclo[4.3.0]non-5-ene salts thereof, or derivatives thereof.

In one preferred embodiment, the process for preparation compound of formula (I) is carried out using a mixture of compounds of formula (IIa) and formula (IIb) in presence of a catalyst selected from 1,8-Diazabicyclo[5.4.0]undec-7-ene or 1,5-Diazabicyclo[4.3.0]non-5-ene or salts thereof, or derivatives thereof.

In one preferred embodiment, the process for preparation compound of formula (I) is carried out by converting a mixture of compounds of formula (IIa) and formula (IIb) into compounds of formula (IIa) which is reacted with the compound of formula (III) in presence of a catalyst selected from 1,8-Diazabicyclo[5.4.0]undec-7-ene or 1,5-Diazabicyclo[4.3.0]non-5-ene or salts thereof, or derivatives thereof.

Typically, the process according to the present invention is carried out using a catalyst selected from 1,8-Diazabicyclo[5.4.0]undec-7-ene and/or 1,5-Diazabicyclo[4.3.0]non-5-ene in an amount from about 0.01 mol % to about 7 mol %, preferably from about 0.1 mol % to about 5 mol %.

In another embodiment the process according to the present invention is carried out using 1,5-Diazabicyclo[4.3.0]non-5-ene, salts and derivatives thereof as a catalyst in an amount from about 0.01 mol % to about 7 mol %.

In another embodiment the process according to the present invention is carried out using 1,5-Diazabicyclo[4.3.0]non-5-ene, salts and derivatives thereof as a catalyst in an amount from about 0.1 mol % to about 5 mol %.

In an embodiment the present process is carried out at a temperature in the range of about 0-150° C. In an embodiment the process is carried out at a temperature in the range of about 30-120° C. In preferred embodiment the process is carried out at a temperature in the range of about 50-120° C.

In an embodiment the process is carried out at a temperature in the range of about 70-100° C. for example 80-90° C.

In an embodiment the process is carried out for a period of about 1 to 12 hrs.

In an embodiment, the process for preparation compound of formula (I)

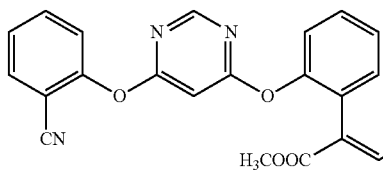

(I)

comprising:
(a) reacting a compound of formula (V) with a compound of formula (IV)

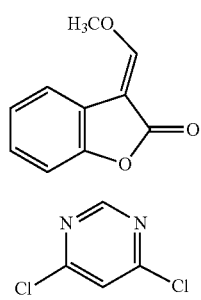

(V)

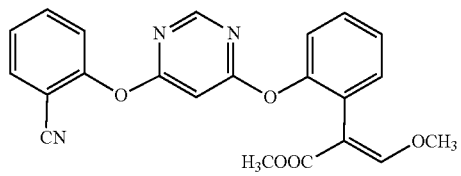

(I)

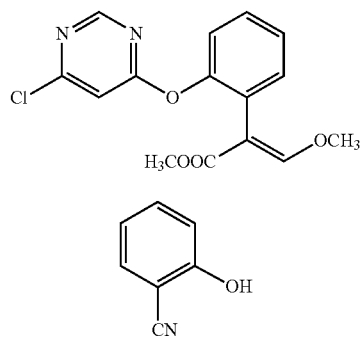

(IV)

comprising:
reacting compound of formula (VI) with compound of formula (V)

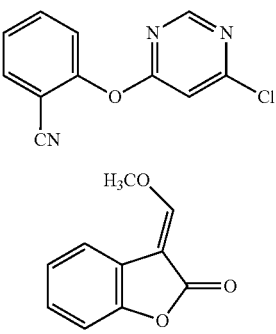

(VI)

in the presence of a catalyst selected from 1,8-Diazabicyclo[5.4.0]undec-7-ene or 1,5-Diazabicyclo[4.3.0]non-5-ene or salts thereof, or derivatives thereof to obtain compounds of formula (IIa);

(b) reacting compounds of formula (IIa) with the compound of formula (III)

(IIa)

(III)

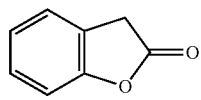

in the presence of a catalyst selected from 1,8-Diazabicyclo[5.4.0]undec-7-ene or 1,5-Diazabicyclo[4.3.0]non-5-ene or salts thereof, or derivatives thereof to obtain compound of formula (I).

In an embodiment, the compound of formula (V) is prepared from compound of formula (VII).

(VII)

In yet another embodiment the compound of formula (V) is prepared starting from the compound of formula (VII) by the known methods for example as described in EP688769.

In an embodiment the present process is carried out at a temperature in the range of about 0-150° C.

In an embodiment the process is carried out at a temperature in the range of about 30-120° C.

In preferred embodiment the process is carried out at a temperature in the range of about 50-120° C.

In an embodiment the process is carried out at a temperature in the range of about 70-100° C. for example 80-90° C.

In an embodiment the process is carried out for a period of about 6 to 30 hrs for example for a period of about 4 to 20 hrs.

In an embodiment, 1,8-Diazabicyclo[5.4.0]undec-7-ene or 1,5-Diazabicyclo[4.3.0]non-5-ene or salts or derivatives thereof is used as catalyst for the preparation of compound of formula (I) and formula (II).

In an embodiment, the present invention provides a process for preparation of compound of formula (I)

(V)

in the presence of a catalyst selected from 1,8-Diazabicyclo[5.4.0]undec-7-ene or 1,5-Diazabicyclo[4.3.0]non-5-ene or salts thereof, or derivatives thereof.

The present invention provides a process for preparation compound of formula (VI)

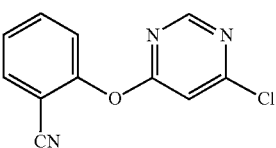

(VI)

comprising
reacting compound of formula (IV) with compound of formula (III)

(IV)

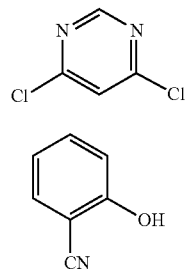

(III)

in the presence of 1,8-Diazabicyclo[5.4.0]undec-7-ene or 1,5-Diazabicyclo[4.3.0]non-5-ene or salts thereof, or derivatives thereof.

In an embodiment, the present invention provides a process for preparation of compound of formula (I)

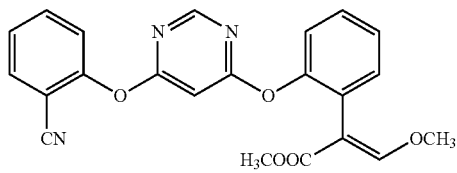

(I)

comprising:

(a) reacting compound of formula (IV) with compound of formula (III)

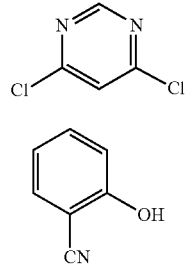

(IV)

(III)

in the presence of 1,8-Diazabicyclo[5.4.0]undec-7-ene or 1,5-Diazabicyclo[4.3.0]non-5-ene or salts thereof, or derivatives thereof to obtain compound of formula (VI);

(b) reacting a compound of formula (VI) with compound of formula (V)

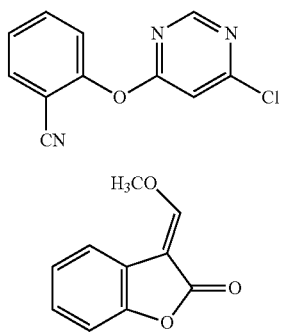

(VI)

(V)

in the presence of a catalyst selected from 1,8-Diazabicyclo[5.4.0]undec-7-ene or 1,5-Diazabicyclo[4.3.0]non-5-ene or salts thereof, or derivatives thereof to obtain a compound of formula (I).

In an embodiment, 1,8-Diazabicyclo[5.4.0]undec-7-ene or 1,5-Diazabicyclo[4.3.0]non-5-ene or salts thereof, or derivatives thereof is used as catalyst for the preparation of compound of formula (I) and formula (VI).

In an embodiment the present invention further provides a process for preparation compound of formula (I)

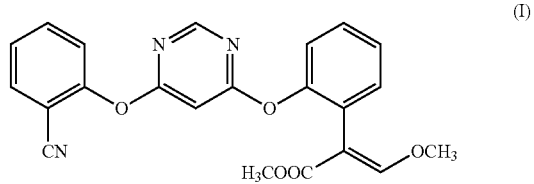

(I)

comprising:

1) reacting compound of formula (IV) with compound of formula (III) in the presence of a catalyst selected from 1,8-Diazabicyclo[5.4.0]undec-7-ene, salts and derivatives thereof or 1,5-Diazabicyclo[4.3.0]non-5-ene, salts and derivatives thereof to obtain compound of formula (VI); and

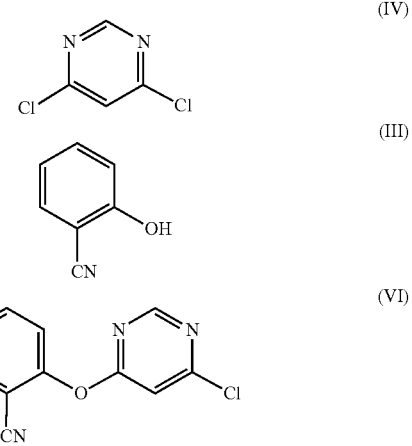

(IV)

(III)

(VI)

2) reacting compounds of formula (VI) with compound of formula (V)

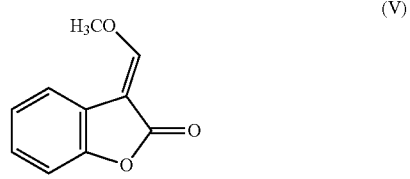

(V)

in the presence of a catalyst selected from 1,8-Diazabicyclo[5.4.0]undec-7-ene, salts thereof, or derivatives thereof or 1,5-Diazabicyclo[4.3.0]non-5-ene, salts thereof, or derivatives thereof to obtain compound of formula (I).

In a preferred embodiment, 1,8-Diazabicyclo[5.4.0]undec-7-ene or 1,5-Diazabicyclo[4.3.0]non-5-ene, or salts thereof, or derivatives thereof is used as catalyst for preparation of compound of formula (I) and formula (VI).

In an embodiment the present process is carried out at a temperature in the range of about 0-150° C.

In an embodiment the process is carried out at a temperature in the range of about 30-120° C.

In preferred embodiment the process is carried out at a temperature in the range of about 50-120° C.

In an embodiment the process is carried out at a temperature in the range of about 70-100° C. for example 80-90° C.

In an embodiment the process is carried out for a period of about 3 to 24 hrs.

Typically, the process for preparation of compound of formula (I) comprises two steps,
1) process for preparing the compound of formula (II) and
2) converting the compound of formula (II) to compound of formula (I).

In an embodiment step (1) and step (2) of the process are carried out in a continuous or stepwise manner In another embodiment step (2) of the process can be carried out with or without isolation of step (1) product.

In an embodiment the step (1) and step (2) of the process can be carried out as one pot reaction to obtain the desired product.

In another preferred embodiment the process for preparation of compound of formula (I) comprises
  (a) reacting 4,6-Dichloropyrimidine with 3-(methoxy methylene)-2(3H)-benzofuranone in presence of catalytic amount of 1,8-Diazabicyclo[5.4.0]undec-7-ene or 1,5-Diazabicyclo[4.3.0]non-5-ene, or salts thereof, or derivatives thereof;
  (b) optionally isolating the product from the reaction mixture;
  (c) optionally purifying the compound by crystallization to obtain pure methyl (E)-2-{2-[6-chloropyrimidin-4-yloxy]phenyl}-3-methoxyacrylate (Compound IIa)
  (d) converting pure (E)-2-{2-[6-chloropyrimidin-4-yloxy]phenyl}-3-methoxyacrylate (Compound IIa) to azoxystrobin.

Typically, the process for preparation of compound of formula (IIa) comprises, reaction of 4,6-Dichloropyrimidine with 3-(methoxy methylene)-2(3H)-benzofuranone in presence of 1,8-diazabicyclo [5,4.0]undec-7-ene or 1,5-Diazabicyclo[4.3.0]non-5-ene, or salts thereof, or derivatives thereof.

The reaction is carried out in presence of base for example potassium carbonate and solvent for example methyl isobutyl ketone.

The reaction is carried out at temperature of about 50 to 75° C.

The product thus formed is optionally isolated from the reaction mixture and crystallised to obtain (E)-2-{2-[6-chloropyrimidin-4-yloxy]phenyl}-3 -methoxyacrylate (Compound IIa).

The compound, (E)-2-{2-[6-chloropyrimidin-4-yloxy]phenyl}-3-methoxyacrylate (Compound IIa) produced according to the present invention is having high purity of at least 96%, and reduced dimer content i.e. below 1% preferably below 0.5%. The compound of formula (IIa) thus obtained is used for preparing the compound of formula (I).

In another preferred embodiment, the process for preparation of compound of formula (I) comprising
  a) reacting 4,6-Dichloropyrimidine with o-cyanophenol in presence of catalytic amount of 1,8-Diazabicyclo[5.4.0]undec-7-ene or 1,5-Diazabicyclo[4.3.0]non-5-ene, or salts or derivatives thereof to obtain 2-[(6-chloro-4-pyrimidinyl)oxy]-benzonitrile (compound VI);
  b) optionally isolating the product from the reaction mixture;
  c) reacting 2-[(6-chloro-4-pyrimidinyl)oxy]-benzonitrile with 3-(methoxy methylene)-2(3H)-benzofuranone in presence of catalytic amount of 1,8-Diazabicyclo[5.4.0]undec-7-ene or 1,5-Diazabicyclo[4.3.0]non-5-ene, or salts thereof, or derivatives thereof to obtain azoxystrobin;
  d) optionally isolating the product from the reaction mixture;
  e) optionally purifying the compound to obtain pure azoxystrobin.

In another preferred embodiment, the process for preparation of azoxystrobin (I) comprises reaction of 3-(methoxy methylene)-2(3H)-benzofuranone with 2-[(6-chloro-4-pyrimidinyl)oxy]-benzonitrile in presence of catalytic amount of 1,8-diazabicyclo [5.4.0] undec-7-ene.

The reaction is carried out in presence of metal alkoxide for example sodium methoxide.

The reaction is carried out at temperature 50 to 75° C.

The product thus formed is isolated from the mixture and optionally the compound thus obtained is crystalized from a solvent selected from alcohol to obtain azoxystrobin Azoxystrobin thus produced according to the present invention is having high purity of at least 98% preferably about 99% and reduced dimer content i.e. below 0.1%.

Accordingly, the process for preparation of fluoxastrobin (IA) comprises
  (a) reacting a compound of formula (IIIa) with a compound of formula (IVa) in presence of catalytic amount of 1,8-Diazabicyclo[5.4.0]undec-7-ene or 1,5-Diazabicyclo[4.3.0]non-5-ene, or salts thereof, or derivatives thereof to get a compound of formula (VIa);

(IIIa)

(IVa)

(VIa)

(b) converting compound of formula (VIa) to fluoxastrobin.

(Ia)

The process of converting compound of formula (VIa) to fluoxastrobin (IA) comprises reacting compounds of Formula (VIa) with compounds of Formula (Va) in presence of in presence of catalytic amount of 1,8-Diazabicyclo[5.4.0]undec-7-ene or 1,5-Diazabicyclo[4.3.0]non-5-ene, or salts thereof, or derivatives thereof.

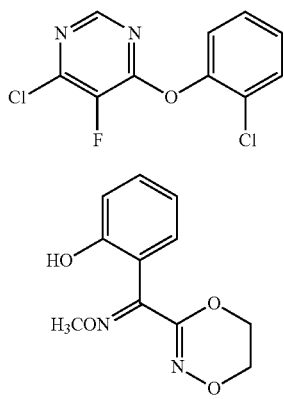

(VIa)

(Va)

According to the present invention the compound of formula (IA) can be prepared in high yield and high purity.

In an embodiment the reactions of the process according to the present invention is carried out in presence of suitable base selected from inorganic bases such as metal hydroxides, carbonates or bicarbonates, or alkoxides, or organic bases such as aliphatic or aromatic amines. The metal of the inorganic base can be an alkali or alkaline earth metal, for example alkali metals such as lithium, sodium, potassium, etc.; and for example alkaline earth metals such as magnesium, calcium, strontium, barium, etc.

In a preferred embodiment the reaction according to the present invention is carried out in presence of carbonates or bicarbonates as a base.

In a preferred embodiment the reaction according to the present invention is carried out in presence of potassium carbonate.

In a preferred embodiment the reaction according to the present invention is carried out in presence of sodium methoxide.

In an embodiment the reaction according to the present invention is carried out in a suitable solvent selected from aliphatic, alicyclic, and aromatic hydrocarbon such as petroleum ether, hexane, heptane, cyclohexane, toluene, xylene, halogenated hydrocarbon such as chloroform, dichloromethane, dichloroethane, chlorobenzene, trichloroethane, esters such as ethyl acetate, methyl acetate, methyl formate, ethyl formate, isopropyl acetate, ethers such as diethyl ether, dimethyl ether, tetrahydrofuran, diisopropylether, methyl-tert-butyl ether, methyl-tert-amyl ether, dioxane, ketones such as acetone, butanone, methyl isobutyl ketone and cyclohexanone, amides such as N,N-dimethylformamide, N,N-dimethylacetamide, N-methylformamide, N-methylpyrrolidone and hexamethylphosphoric triamide, alcohols such as methanol, ethanol, isopropanol and n-propanol or mixtures thereof.

In a preferred embodiment the reaction according to the present invention is carried out in dimethylformamide.

In a preferred embodiment the reaction according to the present invention is carried out in methyl isobutyl ketone.

In an embodiment the present invention provides a process for sufficiently reducing the formation of undesired products/impurity formed during the process of preparation strobilurin compounds like azoxystrobin or their intermediates.

In an embodiment the process according to the present invention provides a compound of formula (I) or a compound of formula (II) that is substantially free of certain impurities.

In an embodiment, the term 'impurities' refers to unreacted synthetic intermediates, reagents, solvents, organic and/or inorganic products of side reactions, products of dimerization of intermediates, organic and/or inorganic salts and/or other undesired materials.

The term "substantially free", referred herein mean that the desired compounds contain less than about 1.0% by weight of the impurity, preferably less than about 0.5% by weight.

In an embodiment the present invention provides a process for reducing the formation of undesired products/impurity formed during the process of the preparation of strobilurin compounds and or their intermediates.

The strobilurin compound of Formula (I) produced in high yield and substantially free of impurities according to the present invention.

Typically, the strobilurin compound of Formula (I) prepared according to the present process have purity greater than 95% preferably greater than 98% by HPLC for example 99%.

Preferably, the processes according to the present invention provide highly pure strobilurin compounds of Formula (I) that are substantially free of impurities; and in particular a dimer impurity below 0.15% by weight. Advantageously, the content of dimer impurity in final azoxystrobin could be reduced up to 0.15% by using the present process as described herein, and which could be reduced to below 0.15% or eliminated completely.

In a preferred embodiment the process according to the present invention provides a compound of formula (I) or a compound of formula (II) that is substantially free of an impurity represented by a compound of formula (X).

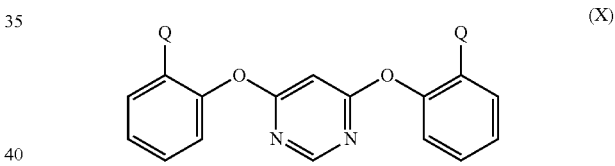

(X)

In an embodiment the process according to the present invention provides a compound of formula I or a compound of formula (II) that is substantially free of an impurity represented by a compound of formula (X) wherein Q is methyl 2-(3,3-dimethoxy)propanoate group, methyl (E)-2-(3-methoxy)acrylate group or a mixture of two compounds.

In an embodiment the process according to the present invention provides a compound of formula I or a compound of formula (II) that contains less than 1% of an impurity represented by a compound of formula (X) wherein Q is methyl 2-(3,3-dimethoxy)propanoate group, methyl (E)-2-(3-methoxy)acrylate group or a mixture of two compounds

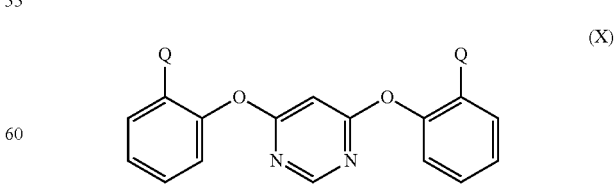

(X)

In an aspect the present invention provides intermediate compound of formula (VI) that is substantially free of impurities which is useful for preparation of highly pure azoxystrobin.

In a preferred embodiment the process according to the present invention provides a compound of formula I or a compound of formula (VI) that is substantially free of an impurity represented by a compound of formula (XI).

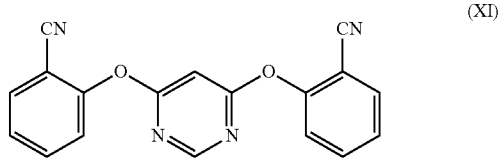

In an embodiment the process according to the present invention provides a compound of formula I or a compound of formula (VI) that contains less than 1% of an impurity represented by a compound of formula (XI).

In an embodiment the compound of formula I is azoxystrobin.

Azoxystrobin produced according to the present invention is having purity at least 99% and reduced content of dimer impurity selected from compound (X) or compound (XI) or combinations thereof preferably less than 0.1% by weight.

The present invention further provides azoxystrobin prepared according to the present invention wherein said azoxystrobin is having a volume average particle size distribution D50 up to 300 μm (micrometers). The particles can be further micronized using conventional methods to reduce the particle size for making suitable formulations.

Advantages of the present invention are
1. The process is an efficient and commercially viable process.
2. The process provides compound of Formula I and compound of formula II that are substantially free of certain impurities
3. The invention provides a process for the preparation of azoxystrobin fungicides in good yield and high purity that is acceptable commercially.

The advantages and other parameters of the present invention is illustrated by the below given examples. However, the scope of the present invention is not limited by the examples in any manner. While the present invention has been described in terms of its specific embodiments, certain modifications and equivalents will be apparent to those skilled in the art and are intended to be included within the scope of the present invention.

EXAMPLES

Example 1

Preparation of Methyl (E)-2-{2-[6-chloropyrimidin-4-yloxy]phenyl}-3-methoxyacrylate (compound IIa)

To a stirred mixture of 3-(methoxy methylene)-2(3H)-benzofuranone (97%, 91 g, 0.5 moles) in methyl formate (275 g), 4,6-dichloropyrimidine (98%, 92 g, 0.605 moles) was added at 10° C. 1,8-diazabicyclo [5,4.0]undec-7-ene (0.038 g, 0.249 mmol, 0.05 mole %) was added to the above reaction mixture followed by drop-wise addition of sodium methoxide (30%, 110 g, 0.61 moles) in methanol at 10 to 15° C. After addition was over, the reaction mass was maintained at 10 to 15° C. for 1 hour. Methyl formate was then distilled off from the mixture while maintaining the temperature below 55° C. Toluene (300 ml) and water (200 ml) were added to the remaining residue and the mixture was stirred at 60-65° C. The mixture was cooled to room temperature and the organic layer was separated. Toluene was distilled off under reduced pressure and the oily residue was heated to 130-135° C. Potassium hydrogen sulphate (1.36 g, 0.01 moles) was added and the reaction mixture was stirred at 130-135° C. under 15-22 mm Hg vacuum for 3 hours. The reaction mixture was cooled to room temperature and diluted with toluene (200 ml). The reaction mixture was washed with water and organic layer was separated. Toluene was distilled off and crude mass was crystalized from methanol (80 ml) to obtain methyl (E)-2-{2-[(6-chloropyrimidin-4-yl)oxy]phenyl}-3-methoxyacrylate, (HPLC purity 98.5%, dimer content: 0.13%).

Example 2

Preparation of Methyl (E)-2-{2-[6-chloropyrimidin-4-yloxy]phenyl}-3-methoxyacrylate (Compound IIa)

To a stirred mixture of 3-(methoxy methylene)-2(3H)-benzofuranone (97%, 91 g, 0.5 moles) in methyl formate (275 g), 4,6-dichloropyrimidine (98%, 92 g, 0.605 moles) was added at 10° C. 1,5-diazabicyclo [4.3.0]non-5-ene (0.031 g, 0.249 mmol, 0.05 mole %) was added to the reaction mixture followed by drop-wise addition of sodium methoxide (30% in methanol 110 g, 0.61 moles) at 10 to 15° C. The reaction mass was maintained at 10 to 15° C. for 1 hour. Methyl formate was then distilled off while maintaining the temperature below 55° C. Toluene (300 ml) and water (200 ml) were added to the residue and the mixture was stirred at 60-65° C. The mixture was cooled to room temperature and the organic layer was separated. Toluene was distilled off under reduced pressure and the oily residue was heated to130-135° C. Potassium hydrogen sulphate (1.36 g, 0.01 moles) was added and the reaction mixture was stirred at 130-135° C. under 15-22mm Hg vacuum for 3 hours. The reaction mixture was cooled to room temperature and diluted with toluene (200 ml). The mixture was washed with water and the organic layer was separated. Toluene was distilled off and crude mass was crystallised from methanol (80 ml) to obtain methyl (E)-2-{2-[(6-chloropyrimidin-4-yl)oxy]phenyl}-3-methoxyacrylate (purity 99%, dimer content: 0.11%)

Example 3 (Comparative example)

Preparation of Methyl (E)-2-{2-[6-chloropyrimidin-4-yloxy]phenyl}-3-methoxyacrylate (IIa) in the Absence of a Catalyst:

To a stirred mixture of 3-(methoxy methylene)-2(3H)-benzofuranone (97%, 91 g, 0.5 moles) in methyl format (275 g), 4,6-dichloropyrimidine (98%, 92 g, 0.605 moles) was added at 10° C. Sodium methoxide (30% in methanol 110 g, 0.61 moles) was dropwise added to this reaction mixture at 10 to 15° C. The reaction mass was maintained at 10 to 15° C. for 1 hour. Methyl formate was distilled off at atmospheric pressure while maintaining the temperature below 55° C. Toluene (300 ml) and water (200 ml) were added to the residue and the mixture was heated to 60-65° C. The mixture was cooled to room temperature and the organic layer was separated. Toluene was distilled off under reduced pressure and the oily residue was heated to 130-135° C. Potassium hydrogen sulphate (1.36 g, 0.01 moles) was added to the mixture and reaction mass was stirred at 130-135° C. under 15-22mm Hg vacuum for 3 hours. The reaction mixture was then cooled to room temperature and diluted with toluene (200 ml). The mixture was washed with water and the organic layer was separated. Toluene was distilled off and crude mass was crystallised from methanol (80 ml) to obtain methyl (E)-2-{2-[(6-chloropyrimidin-4-yl)oxy]phenyl}-3 -methoxyacrylate (purity: 75%, dimer content: 2.6%).

Example 4

Preparation of Azoxystrobin (Compound I)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles) and 2-cyanophenol (33.8 g, 0.275 moles) in DMF (170 g), 1,8-diazabicyclo [5,4.0]undec-7-ene (0.76 g, 0.005 moles, 0.02 mole %) in DMF (10 ml) was added at room temperature. The mixture was heated to 90° C. and stirred at same temperature for 7-8 hours. The reaction mixture was cooled to 50-55° C. and filtered to remove the salt. The filtrate was subjected to distillation to recover DMF at 70-80° C. under vacuum. The residual mass was crystalized from mixture of methanol (90 ml) and water (10 ml) to obtain the titled product (purity: 99.4%, dimer content: 0.05%).

Example 5

Preparation of Azoxystrobin (Compound I)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles) and 2-cyanophenol (33.8 g, 0.275 moles) in DMF (170 g), 1,5-diazabicyclo [4.3.0]non-5-ene (0.62 g, 0.005 moles, 0.02 mole %) in DMF (10 ml) was added at room temperature. The mixture was heated to 90° C. and maintained at same temperature for 7-8 hours. The reaction mixture was cooled to 50-55° C. and filtered to remove the salt. The filtrate was distilled to recover DMF at 70-80° C. under vacuum. The residual mass was crystalized from mixture of methanol (90 ml) and water (10 ml) to obtain the titled product (purity is 99%, dimer content: 0.08%).

Example 6

Preparation of Azoxystrobin (Compound I)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles), 2-cyanophenol (33.8 g, 0.275 moles) in DMF (170 g), catalytic amount of 1,8-diazabicyclo [5,4.0]undec-7-ene (0.38 g, 0.0025 moles, 1 mole %) in DMF (10 ml) was added at room temperature. The mixture was heated to 90° C. and stirred at same temperature for 7-8 hours. The reaction mixture was cooled to 50-55° C. and filtered to remove the salt. The filtrate was distilled to recover DMF at 70-80° C. under vacuum. The residual mass was crystalized from mixture of methanol (90 ml) and water (10 ml) to obtain the titled product (purity: 99.4%, dimer content: 0.05%)

Example 7

Preparation of Azoxystrobin (Compound I)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles) and 2-cyanophenol (33.8 g, 0.275 moles) in DMF (170 g), catalytic amount of 1,5-diazabicyclo [4.3.0]non-5-ene (0.31 g, 0.0025 moles, 1.0 mole %) in DMF (10 ml) was added. The mixture was heated to 90° C. and maintained at same temperature for 7-8 hours. The reaction mixture was cooled to 50-55° C. and filtered to remove the salt.

The filtrate was distilled to recover DMF at 70-80° C. under vacuum. The residual mass was crystalized from mixture of methanol (90 ml) and water (10 ml) to obtain the titled product (purity: 99%, dimer content: 0.06%).

Example 8

Preparation of Azoxystrobin (Compound I)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles) and 2-cyanophenol (33.8 g, 0.275 moles) in DMF (170 g), catalytic amount of 1,8-diazabicyclo [5,4.0]undec-7-ene (0.0038 g, 0.025 mmoles, 0.01 mole %) in DMF (10 ml) was added at room temperature. The mixture was heated to 90° C. and stirred at same temperature for 7-8 hours. The reaction mixture was cooled to 50-55° C. and filtered to remove the salt. The filtrate was distilled to recover DMF at 70-80° C. under vacuum. The residual mass was crystalized from mixture of methanol (90 ml) and water (10 ml) to obtain the titled product (purity: 99.4%, dimer content: 0.05%)

Example 9

Preparation of Azoxystrobin (Compound I)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles) and 2-cyanophenol (33.8 g, 0.275 moles) in DMF (170 g), catalytic amount 5-diazabicyclo [4.3.0]non-5-ene (0.0031 g, 0.025 mmoles, 0.01 mole %) in DMF (10 ml) was added at room temperature. The mixture was heated to 90° C. and maintained at same temperature for 7-8 hours. The reaction mixture was cooled to 50-55° C. and filtered to remove the salt. The filtrate was distilled to recover DMF at 70-80° C. under vacuum. The residual mass was crystalized from mixture of methanol (90 ml) and water (10 ml) to obtain the titled product (purity: 99%, dimer content: 0.06%).

Example 10

Preparation of 2-[(6-chloro-4-pyrimidinyl)oxy]-benzonitrile (Compound VI)

A mixture of 4,6-Dichloropyrimidine (98%, 92 g, 0.605 moles), potassium carbonate (104.5 g, 0.756 moles) and 1,5-diazabicyclo [4.3.0]non-5-ene (0.038 g, 0.3 mmol, 0.05 mole %) was stirred in methyl isobutyl ketone (240 ml) at 60 to 65° C. O-cyanophenol (70.57g, 0.593 moles) in methyl isobutyl ketone (200 ml) was added dropwise to the mixture. The mixture was stirred at 60° C. for 6 hours and then cooled, the organic phase was separated and washed with 5% NaOH, the aqueous phase was extracted with methyl isobutyl ketone, the combined organic extract was dried over sodium sulphate and solvent was partially distilled to obtain the product. The product is crystallised, filtered and dried to get pure 2-[(6-chloro-4-pyrimidinyl)oxy]-benzonitrile (purity: 97%, dimer: 0.14%).

Example 11:

Preparation of Azoxystrobin (Compound I)

To a stirred mixture of 3-(methoxy methylene)-2(3H)-benzofuranone (97%, 181.4 g, 1.0 moles) in methyl formate (566 g), 2-[(6-chloro-4-pyrimidinyl)oxy]-benzonitrile (96.6%, 251.6 g, 1.05 moles) was added at 10-15° C. Catalytic amount of 1,5-diazabicyclo [4.3.0]non-5-ene (0.062 g, 0.5 mmol, 0.05 mole %) was added to the mixture followed by dropwise addition of sodium methoxide (30% in methanol, 219 g, 1.22 moles) at 10 to 15° C. After addition was over, the reaction mass was maintained at 10 to 15° C. for 1 hour. Methyl formate was then distilled off while maintaining the temperature between 55-65° C. Toluene (700 ml) and water (400 ml) were added to the residue and the mixture was heated to 65-70° C. with stirring for 1 hour. The mixture was cooled to room temperature and the organic layer was separated. Toluene was distilled off under reduced pressure and the oily residue was heated to 78-80° C. To this residue acetic anhydride was dropwise added at 78-80° C. and the mixture was cooked for 30 minutes. To the reaction mixture, methane sulphonic acid (8 g) was added dropwise and mixture was stirred for 3 hours. After completion of reaction, the mass was diluted with water (250 ml) and the mixture was heated to 65-70° C. for 30 minutes. The organic layer was washed with 10% sodium bicarbonate (200 ml), organic layer was separated, dried and concentrated at reduced pressure. The residual mass thus obtained was crystallised from methanol (450 ml) to get the titled product (purity: 99.4%, dimer content: 0.05%).

Example 12

Preparation of 2-[(6-chloro-4-pyrimidinyl)oxy]-benzonitrile (Compound VI)

A mixture of 4,6-Dichloropyrimidine (98%, 92 g, 0.605 moles), potassium carbonate (104.5 g, 0.756 moles), 1,8-diazabicyclo [5,4.0]undec-7-ene (0.046 g, 0.3 mmol, 0.05 mole %) was stirred in methyl isobutyl ketone (240 ml) at 60 to 65° C. To this mixture o-cyanophenol (70.57 g, 0.593 moles) in methyl isobutyl ketone (200 ml) was dropwise added. The mixture was heated to 60° C. and stirred for 6 hours and then cooled, the organic phase was separated and washed with 5% NaOH, the aqueous phase was extracted with methyl isobutyl ketone, the combined organic extract was dried over sodium sulphate and the solvent was partially distilled. The product thus obtained was crystallised, filtered and dried to get 2-[(6-chloro-4-pyrimidinyl)oxy]-benzonitrile (purity: 96.6%, dimer: 0.14%).

Example 13

Preparation of Azoxystrobin (Compound I)

To a stirred mixture of 3-(methoxy methylene)-2(3H)-benzofuranone (97%, 181.4 g, 1.0 moles) in methyl formate (566 g), 2-[(6-chloro-4-pyrimidinyl)oxy]-benzonitrile (96.6%, 251.6 g, 1.05 moles) was added at 10-15° C. To the reaction mixture catalytic amount of 1,8-diazabicyclo [5,4.0]undec-7-ene (0.076 g, 0.5 mmol, 0.05 mole %) was added followed by drop-wise addition of sodium methoxide (30% in methanol, 219 g, 1.22 moles) at 10 to 15° C. and the reaction mass was maintained at 10 to 15° C. for 1 h. Methyl formate was then distilled off while maintaining the temperature between 55-65° C. Toluene (700 ml) and water (400 ml) were added to the reaction mass and the mixture was heated to 65-70° C. The mixture was cooled to room temperature and the organic layer was separated. Toluene was distilled off under reduced pressure and the oily residue was heated to 78-80° C. To this residue acetic anhydride was drop-wise added at 78-80° C. and the mixture was cooked for 30 minutes. To this mixture methane sulphonic acid (8 g) was added dropwise and the mixture was stirred for 3 hours. After completion of reaction, the mass was diluted with water (250 ml) and the mixture was heated 65-70° C. for 30 minutes. The organic layer was washed with 10% sodium bicarbonate (200 ml), separated organic layer was dried and concentrated at reduced pressure. The residual mass was crystallised from methanol (450 ml) to obtain the titled product (purity: 99.1%, dimer content: 0.07%).

Example 14 (Comparative Example)

Preparation of 2-[(6-chloro-4-pyrimidinyl)oxy]-benzonitrile(Compound of Formula VI)

A mixture of 4,6-Dichloropyrimidine (98%, 92 g, 0.605 moles) and potassium carbonate (104.5 g, 0.756 moles) in methyl isobutyl ketone (240 ml) was stirred at 60 to 65° C. To this mixture o-cyanophenol (70.57 g, 0.593 moles) in methyl isobutyl ketone (200 ml) was added dropwise. The mixture was heated to 60 to 65° C. and stirred for 8 hours and then cooled, the organic phase was separated and washed with 5% NaOH, the aqueous phase was extracted with methyl isobutyl ketone, the combined organic extract was dried over sodium sulphate and the solvent was partially distilled. The product thus obtained was crystallised, filtered and dried to get 2-[(6-chloro-4-pyrimidinyl)oxy]-benzonitrile (purity: 76%, dimer: 5.2%).

We claim:
1. A process for preparation of a strobilurin compound of formula (I) comprising the steps of:
(a) preparing a compound of formula (II) by reacting a compound of formula (V) with a compound of formula (IV)

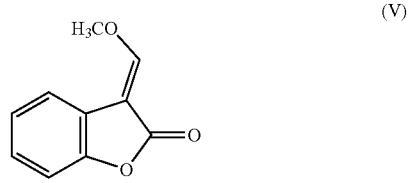 [SMILES: CO/C=C1/C(=O)Oc2ccccc21]

(V)

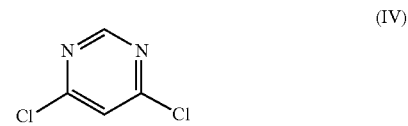

(IV)

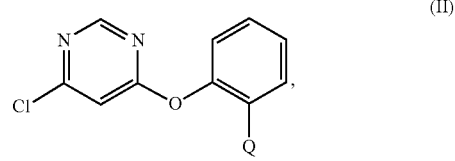

(II)

wherein Q is selected from methyl (E)-2-(3-methoxy) acrylate and methyl 2-3,3-dimethoxy) propanoate, and in the presence of a catalyst selected from 1,8-diazabicyclo[5.4.0]undec-7-ene, 1,5-diazabicyclo[4.3.0]non-5-ene, salts thereof, or derivatives thereof, and (b) reacting said compound of formula (II) with a compound of formula (III) in the presence of said catalyst

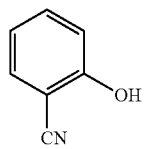
(III)

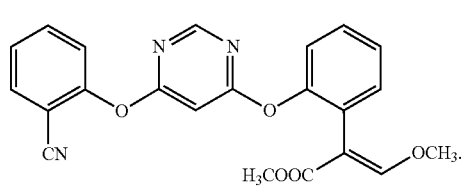
(I)

2. The process as claimed in claim 1, wherein said compound of formula (II) is selected from

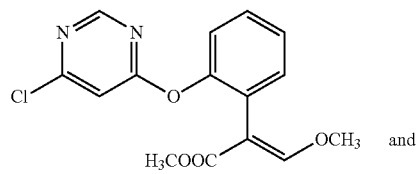
(IIa)
and

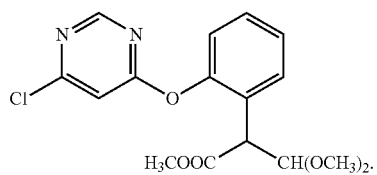
(IIb)

3. The process as claimed in claim 1, wherein said compound of formula (II) is a mixture of said compound of formula (IIa) and said compound of formula (IIb)

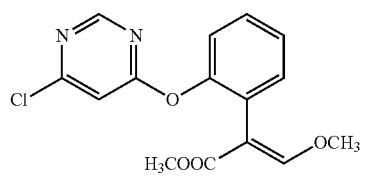
(IIa)

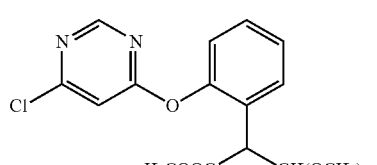
(IIb)

4. A process for preparation of compound of formula (I) comprising the steps of:

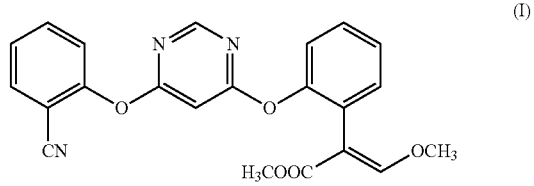
(I)

(a) preparing the compound of formula (VI) by reacting the compound of formula (IV) with a compound of formula (III) in the presence of a catalyst selected from 1,8-diazabicyclo[5.4.0]undec-7-ene, 1,5-diazabicyclo[4.3.0]non-5-ene, salts thereof, or derivatives thereof, and

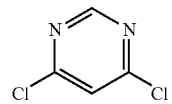
(IV)

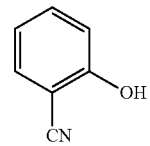
(III)

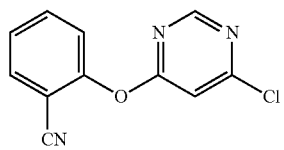
(VI)

(b) reacting the compound of formula (VI) with the compound of formula (V)

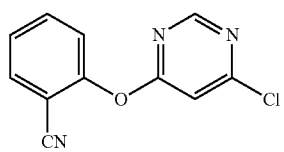
(VI)

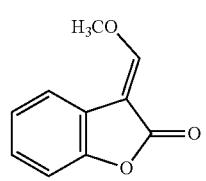
(V)

to obtain the compound of formula (I).

5. The process as claimed in claim 1, wherein said catalyst is selected from 1,8-diazabicyclo[5.4.0]undec-7-ene or derivatives thereof represented by formulae (VIII), (VIIIa) and (VIIIb), wherein R is selected from hydrogen, hydroxyl, $C_1$-$C_{20}$ hydrocarbonyl, amino, $C_1$-$C_6$ alkyl amino, cyano or halogen

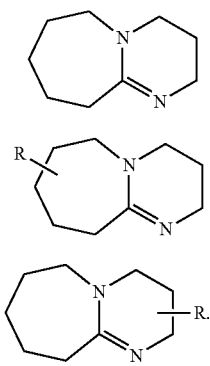

(VIII)

(VIIIa)

(VIIIb)

6. The process according to claim 1, wherein said process is carried out in the presence of said catalyst selected from 1,5-diazabicyclo[4.3.0]non-5-ene or derivatives thereof represented by formulae (IX), (IXa) and (IXb), wherein R is selected from hydrogen, hydroxyl, $C_1$-$C_{20}$ hydrocarbonyl, amino, $C_1$-$C_6$ alkyl amino, cyano or halogen

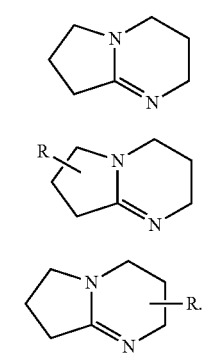

(IX)

(IXa)

(IXb)

7. The process as claimed in claim 1, wherein said catalyst is used in an amount from about 0.01 mol % to about 7 mol %.

8. The process as claimed in claim 1, wherein said process is carried out at a temperature in the range of 0-150 ° C. for 1 to 24 hrs.

9. The process as claimed in claim 1, wherein said process is carried out in presence of solvent and base.

10. The process as claimed in claim 9, wherein said base is selected from metal hydroxides, carbonates, bicarbonates, alkoxides, aliphatic amines, or aromatic amines.

11. The process as claimed in claim 9, wherein said solvent is petroleum ether, hexane, heptane, cyclohexane, toluene, xylene, chloroform, dichloromethane, dichloroethane, chlorobenzene, trichloroethane, ethyl acetate, methyl acetate, methyl formate, ethyl formate, isopropyl acetate, diethyl ether, dimethyl ether, tetrahydrofuran, diisopropyl ether, methyl-tert-butyl ether, methyl-tert-amyl ether, dioxane, acetone, butanone, methyl isobutyl ketone, cyclohexanone, N,N-dimethylformamide, N,N-dimethylacetamide, N-methylformamide, N-methyl-pyrrolidone, hexamethylphosphoric triamide, methanol, ethanol, isopropanol, n-propanol, or mixtures thereof.

12. A process for preparation of a compound of formula (I) as claimed in claim 1 comprising the steps of:
(a) reacting 4,6-dichloropyrimidine with 3-(methoxy methylene)-2(3H)-benzofuranone in presence of a catalytic amount of 1,8-diazabicyclo[5.4.0]undec-7-ene, 1,5-diazabicyclo[4.3.0]non-5-ene, or a salt thereof, or derivative thereof;
(b) optionally isolating the product of step (a);
(c) purifying the product of steps (a) or (b) to obtain pure methyl (E)-2-{2-[6-chloropyrimidin-4-yloxy] phenyl}-3-methoxyacrylate (compound of formula (IIa)), and
(d) converting pure methyl (E)-2-{2-[6-chloropyrimidin-4-yloxy]phenyl}-3-methoxyacrylate from (c) (compound of formula (IIa)) to azoxystrobin.

13. The process as claimed in claim 12, wherein said step (d) comprises reacting methyl (E)-2-{2-[6-chloropyrimidin-4-yloxy] phenyl}-3-methoxyacrylate (Compound IIa) with o-cyanophenol in presence of a catalytic amount of 1,8-diazabicyclo[5.4.0]undec-7-ene or 1,5-diazabicyclo[4.3.0] non-5-ene, salts thereof or derivatives thereof to obtain azoxystrobin (compound of formula (I)).

14. A process for preparation of a compound of formula (I) as claimed in claim 4 comprising the steps of:
(a) reacting 4,6-dichloropyrimidine with o-cyanophenol in presence of a catalytic amount of 1,8-diazabicyclo [5.4.0]undec-7-ene, or 1,5-diazabicyclo[4.3.0]non-5-ene, or salts thereof, or derivatives thereof to obtain 2-[(6-chloro-4-pyrimidinyl)oxy]-benzonitrile;
(b) optionally isolating the product of step (a) from the reaction mixture;
(c) reacting the 2-[(6-chloro-4-pyrimidinyl)oxy]-benzonitrile with 3-(methoxy methylene)-2(3H)-benzofuranone in presence of catalytic amount of 1,8-diazabicyclo[5.4.0]undec-7-ene, or 1,5-diazabicyclo[4.3.0]non-5-ene, or a salt thereof, or derivative thereof to obtain azoxystrobin;
(d) optionally isolating the product of step (c) from the reaction mixture; and
(e) optionally purifying the product of step (d) to obtain pure compound of formula (I) (azoxystrobin).

15. A compound of formula (II) as prepared by the process of claim 1 having purity of at least 96%, and that is substantially free of impurities represented by a compound of formula (X) wherein Q is a methyl 2-(3,3-dimethoxy) propanoate group, a methyl (E)-2-(3-methoxy)acrylate group or a combination of the two groups

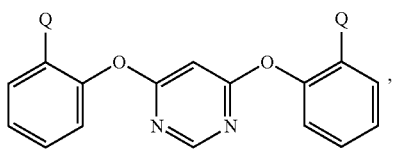

(X)

16. A process for preparation of a strobilurin compound of formula (I) comprising the steps of:
(a) preparing a compound of formula (II) by reacting a compound of formula (V) with a compound of formula (IV)

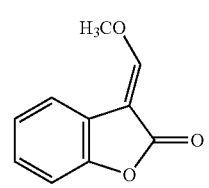

(V)

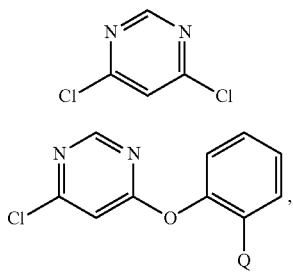

(IV)

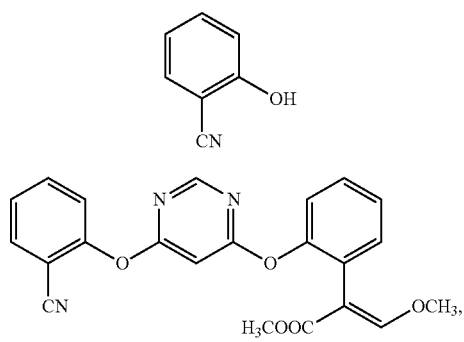

(II)

wherein Q is selected from methyl (E)-2-(3-methoxy) acrylate and methyl 2-3,3-dimethoxy) propanoate, and in the presence of a catalyst selected from 1,8-diazabicyclo[5.4.0]undec-7-ene, 1,5-diazabicyclo[4.3.0]non-5-ene, salts thereof, or derivatives thereof, and (b) reacting said compound of formula (II) with a compound of formula (III) in the presence of said catalyst (III)

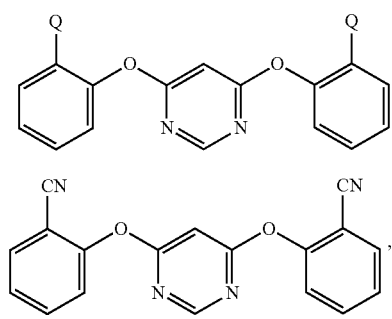

(I)

wherein said strobilurin compound of formula (I) has a purity of at least 99%, and a reduced content of dimer impurity selected from compound (X), compound (XI), and combination thereof of less than 0.1% by weight (X)

(XI)

wherein Q is a methyl 2-(3,3-dimethoxy)propanoate group, a methyl (E)-2-(3-methoxy)acrylate group, or a combination of the two groups.

17. The process as claimed in claim 4, wherein said catalyst is selected from 1,8-diazabicyclo[5.4.0]undec-7-ene or derivatives thereof represented by formulae (VIII), (VIIIa) and (VIIIb), wherein R is selected from hydrogen, hydroxyl, $C_1$-$C_{20}$hydrocarbonyl, amino, $C_1$-$C_6$ alkyl amino, cyano or halogen

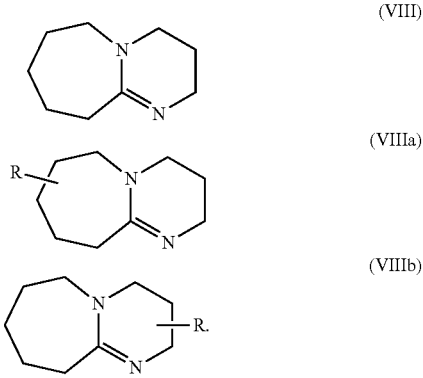

(VIII)

(VIIIa)

(VIIIb)

18. The process according to claim 4, wherein said process is carried out in the presence of said catalyst selected from 1,5-diazabicyclo[4.3.0]non-5-ene or derivatives thereof represented by formulae (IX), (IXa) and (IXb), wherein R is selected from hydrogen, hydroxyl, $C_1$-$C_{20}$ hydrocarbonyl, amino, $C_1$-$C_6$ alkyl amino, cyano or halogen

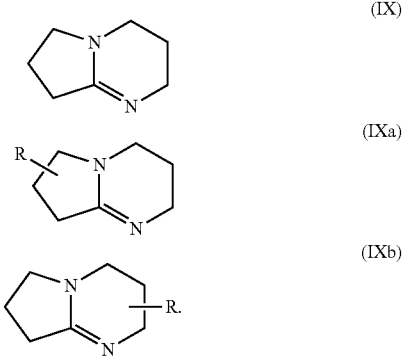

(IX)

(IXa)

(IXb)

19. The process as claimed in claim 4, wherein said catalyst is used in an amount from about 0.01 mol % to about 7 mol %.

20. The process as claimed in claim 4, wherein said process is carried out at a temperature in the range of 0-150 °C. for 1 to 24 hrs.

* * * * *